United States Patent [19]

Esposito et al.

[11] Patent Number: 5,681,548
[45] Date of Patent: Oct. 28, 1997

[54] ORAL FORMULATIONS

[75] Inventors: Anthony Esposito, Roselle; Ernest Kelly, New Brunswich; John Afflitto, Brookside; Abdul Gaffar, Princeton, all of N.J.

[73] Assignee: Colgate Palmolive Company, New York, N.Y.

[21] Appl. No.: 413,022

[22] Filed: Mar. 29, 1995

Related U.S. Application Data

[63] Continuation of Ser. No. 275,853, Jul. 15, 1994, abandoned.

[51] Int. Cl.⁶ .............................. A61K 7/16; A61K 7/18; A61K 7/22; A61K 7/26
[52] U.S. Cl. ............................ 424/49; 424/52; 424/54; 424/58
[58] Field of Search ............................ 424/49–58

[56] References Cited

U.S. PATENT DOCUMENTS

| | | |
|---|---|---|
| 3,164,524 | 1/1965 | Fand et al. . |
| 4,130,637 | 12/1978 | Bauman et al. . |
| 4,490,353 | 12/1984 | Crawford et al. . |
| 4,574,081 | 3/1986 | Shymon et al. . |
| 4,627,977 | 12/1986 | Gaffer et al. . |
| 4,749,562 | 6/1988 | Lane et al. . |
| 4,894,220 | 1/1990 | Nabi et al. . |
| 5,192,531 | 3/1993 | Gaffer et al. . |
| 5,256,401 | 10/1993 | Duckenfield et al. .................. 424/49 |

FOREIGN PATENT DOCUMENTS

| | | | |
|---|---|---|---|
| 0244363 | 4/1987 | European Pat. Off. . | |
| 0259249 | 9/1988 | European Pat. Off. . | |
| 0338978 | 10/1989 | European Pat. Off. . | |
| 0497476 | 5/1992 | European Pat. Off. . | |
| 0497476 | 8/1992 | European Pat. Off. ......... | A61K 7/16 |
| 930725 | 4/1993 | European Pat. Off. . | |
| 0577238 | 5/1994 | European Pat. Off. . | |
| 676324 | 1/1995 | Switzerland ..................... | A61K 7/26 |
| 93/08792 | 5/1993 | WIPO . | |
| 94/16674 | 8/1994 | WIPO . | |
| 9501173 | 1/1995 | WIPO .............................. | A61K 7/16 |
| 9517879 | 7/1995 | WIPO .............................. | A61K 7/16 |

OTHER PUBLICATIONS

American Journal of Dentistry, vol. 3, Sep. 1990 Williams et al., "In Vitro Antiplaque Effects of a Triclosan/Copolymer Mouthrinse".

Katsvtav Sunstar Ca. 114:1200S of JP 02001402 (Jan. 5, 1990) B+T toothpaste.

Murishima/Lion CA. 119:12486S of JP 05124943 (May 21, 1993) A+T dentifice. M.W.

*Primary Examiner*—Shep K. Rose
*Attorney, Agent, or Firm*—Robert L. Stone; Paul Shapiro

[57] ABSTRACT

Oral compositions comprising the combination of an effective surface tension reducing amount of an amphoteric surfactant and an effective antimicrobial amount of a blend of phenolic agents is disclosed. These compositions are indicated in the management or control of dental plaque.

11 Claims, No Drawings

ORAL FORMULATIONS

FIELD OF THE INVENTION

This application is a continuation of application Ser. No. 08/275,853, filed Jul. 15, 1994, abandoned concurrently with the filing of this application.

This invention relates to oral compositions. More particularly, it relates to oral compositions such as mouthrinse, mouthwash, toothpaste, gel dentifrice, tooth powder, chewing gum, lozenge and the like for the control or management of dental plaque and gingivitis. These oral compositions comprise as active ingredients the combination of an amphoteric surfactant, phenolic flavors (agents) and substantially water insuluble noncationic antibacterial agent such as Triclosan in an orally acceptable vehicle forming the desired dosage forms. These compositions may optionally contain other types of surfactants to improve the efficacy, e.g., wetting.

BACKGROUND OF THE INVENTION

Dental plaque is a soft deposit which may form on any part of the tooth surface whereas calculus is a hard mineralized formation. Plaque has been implicated in gingival inflammation (gingivitis). Gingivitis, if untreated, could lead to other complications such as periodontitis and eventually the loss of teeth. Consequently, many measures, in addition to regular tooth brushings, have been proposed as a means of removing dental plaque thereby reducing the incidents of gingivitis. These include, for example, rinsing the mouth with oral compositions containing antiplaque or antimicrobial agents, alone or in combination with phenolic flavors.

DESCRIPTION OF PRIOR ART

U.S. Pat. No. 4,749,562 discloses dentifrice compositions comprising the combination of an anionic surfactant and an antiplaque agent or a zinc salt. Among the anionic surfactants mentioned are sodium lauryl sulfate, sodium lauroyl sarcosinate. Dr. Gaffar, et al. teaches in U.S. Pat. No. 4,627,977 anticalculus compositions comprising, as an anticalculus agent a linear molecularly dehydrated polyphosphate salt and to inhibit enzymatic hydrolysis of the polyphosphate salt in saliva, a combination of a fluoride ion-providing source and a synthetic linear polymeric carboxylate. According to U.S. Pat. No. 4,627,977 organic surface-active agents are used to achieve increased prophylactic action, assist in achieving thorough and complete dispersion of the anticalculus agent throughout the oral cavity. These organic surface active-materials may be anionic, nonionic or ampholytic in nature.

Oral antiseptic compositions comprising a combination of boric acid, benzoic acid, menthol, methyl salicylate, thymol and eucalyptol are described in U.S. Pat. No. 3,164,524. The use of a water-insoluble noncationic antibacterial agent such as triclosan is taught for example in several U.S. Pat. Nos., such as 4,894,220; 4,002,880 and 4,749,562; Finally, *The American Journal of Dentistry*, Vol. 3, Special Edition Sept. 1990, page 53, describes the antiplaque effects of a triclosan and a copolymer mouthrinse.

While the art has taught the combination of amphoteric agents with anticalculus compounds, and it has also taught the use of phenolic agents or antimicrobial agents as flavoring agents in oral compositions, we are not aware of any disclosure or suggestion that by combining an amphoteric agent with a phenolic flavor and a substantially water insoluble noncationic antibacterial agent would yield a composition having a greatly improved activity in inhibiting the formation of dental plaque than employing any of these classes of compounds alone.

SUMMARY OF THE INVENTION

Broadly speaking, the present invention relates to oral compositions useful for the management or control of plaque formation on the tooth surfaces. These compositions are based on the findings that a combination of an amphoteric surfactant with a blend of phenolic flavors and a substantially water insuluble noncationic antibacterial agent, as described more fully below, exhibit enhanced efficiency to inhibit dental plaque formation than either of the ingredients used alone. To broaden the therapeutic spectrum, these compositions may optionally contain other known therapeutic agents, e.g., orally acceptable anti-plaque antimicrobial agents. To facilitate even greater efficacy, other types of surfactants, e.g., anionic or cationic agents may also be incorporated into the present compositions.

DETAILED DESCRIPTION OF THE INVENTION

In accordance with the present invention, there are provided oral compositions which comprise in combination an effective surface tension lowering amount of an amphoteric agent and a sufficient antimicrobial amount of a blend of phenolic agents (flavors) and a substantially water insoluble noncationic antibacterial agent.

While amphoteric agents comprise a diverse group of compounds, such as polypeptides, proteins, phospholipids and betaines, we have found the alkyl betaines, e.g., alkyl dimethyl betaines which include decyl betaine or 2-(N-decyl-N,N-dimethylammonio) acetate, myristyl betaine, palmityl betaine, lauryl betaine, cetyl betaine, stearyl betaine, etc., are particularly suitable for the present invention.

Betaine is present in the oral composition in an effective surface tension reducing amount typically from about 0.01% to about 2% by weight. Depending on the dosage form of the oral composition selected, we have found about a 2% by weight of betaine is particularly suitable when the dosage form is a solid such as toothpaste, tooth powder, gel dentifrice, lozenge, chewing gum, tablets, breath fresheners and the like. For oral compositions in liquid form, such as mouthwash or mouth rinse, we have found from about 0.3% w/v to about 0.5% w/v of betaine is particularly suitable.

"Phenolic agents" as that term is employed in this specification and in the claims, describes those compounds which include phenolic groups, or derivatives thereof, which are orally acceptable and which have an acceptable flavor, which is preferably like that of the preferred flavors of the working example formulas that will be given subsequently in this specification.

Such agents are selected from the group consisting of eucalyptol, thymol, methyl salicylate, menthol, chlorothymol and phenol, and halogenated and other derivatives thereof, with the first six being more preferred, and the first four being even more preferred. Although any of such phenolic flavors may be employed alone it may normally be preferred to utilize mixtures of two or more thereof and preferably all four (of the first four listed) will be in the final flavor composition. In such composition it is desirable that there be at least about 5% of each of such four flavors in the total flavor, preferably at least about 10%, and more preferably at least about 15% of each. A much preferred composition includes about 35% of eucalyptol, about 27% of thymol, about 21% of methyl salicylate and about 17% of menthol.

Other phenolic agents and derivatives which may be advantageously employed in this invention include:

Phenol and its Homologs

Phenol
Methyl—Phenol
Methyl—Phenol
Methyl—Phenol
Ethyl—Phenol
2,4-Dimethyl—Phenol
2,4-Dimethyl—Phenol
3,4-Dimethyl—Phenol
2,6-Dimethyl—Phenol
4-n Propyl—Phenol
4-n-Butyl—Phenol
4-n Amyl—Phenol
4-tert-Amyl—Phenol
4-n-Hexyl—Phenol
4-n-Heptyl—Phenol
2-Methoxy-4-(2-Propenyl)-Phenol (Eugenol)

Mono- and Poly-Alkyl and Aralkyl Halophenols

Methyl—p-Chlorophenol
Ethyl—p-Chlorphenol
n-Propyl—p-Chlorophenol
n-Butyl—p-Chlorophenol
n-Amyl—p-Chlorophenol
sec-Amyl—p-Chlorophenol
n-Hexyl—p-Chlorophenol
Cyclohexy—p-Chlorophenol
n-Heptyl—p-Chlorophenol
n-Octyl—p-Chlorophenol
o-Chlorophenol
Methyl—o-Chlorophenol
Ethyl—o-Chlorophenol
n-Propyl—o-Chlorophenol
n-Butyl—o-Chlorophenol
n-Amyl—o-Chlorophenol
tert-Amyl—o-Chlorophenol
n-Hexyl—o-Chlorophenol
n-Heptyl—o-Chloropenol
p-Chlorophenol
o-Benzyl—p-Chlorophenol
o-Benzyl-m-methyl—p-Chlorophenol
o-Benzyl-m, m-dimethyl—p-Chlorophenol
o-Phenylethyl—p-Chlorophenol
o-Phenylethyl-m-methyl—p-Chlorophenol
3-Methyl—p-Chlorophenol
3,5-Dimethyl—p-Chlorophenol
6-Ethyl-3-methyl—p-Chlorophenol
6-n-Propyl-3-methyl—p-Chlorophenol
6-iso Propyl-3-methyl—p-Chlorophenol
2-Ethyl-3,5-dimethyl—p-Chlorophenol
6-sec Butyl-3-methyl—p-Chlorophenol
2-iso-Propyl-3,5-dimethyl—p-Chlorophenol
6-Diethylmethyl-3-methyl—p-Chlorophenol
6-iso-Propyl-2-ethyl-3-methyl—p-Chlorophenol
2-sec Amyl-3,5-dimethyl—p-Chlorophenol
2-Diethylmethyl-3,5-dimethyl—p-Chlorophenol
6-sec Octyl-3-methyl—p-Chlorophenol
p-Bromophenol
Methyl—p-Bromophenol
Ethyl—p-Bromophenol
n-Propyl—p-Bromophenol
N-Butyl—p-Bromophenol
n-Amyl—p-Bromophenol
sec-Amyl—p-Bromophenol
n-Hexyl—p-Bromophenol
cyclohexyl—p-Bromophenol
o-Bromophenol
tert-Amyl—o-Bromophenol
n-Hexyl—o-Bromophenol
N-Propyl-m,m-Dimethyl—o-Bromophenol-Phenyl Phenol
4-Chloro-2-methyl phenol
4-chloro-3-methyl phenol
4-chloro-3,5-dimethyl phenol
2,4-dichloro-3,5-dimethyl phenol
3,4,5,6-tetrabromo-2 methyphenol
5-methyl-2-pentylphenol4-isopropyl-3-methylphenol
5-chloro-2-hydroxydiphenyl methane Resorcinol and its Derivatives Resorcinol
Methyl—Resorcinol
Ethyl—Resorcinol
n-Propyl—Resorcinol
N-Butyl—Resorcinol
n-Amyl—Resorcinol
n-Hexyl—Resorcinol
n-Heptyl—Resorcinol
n-Octyl—Resorcinol
n-Nonyl—Resorcinol
Phenyl—Resorcinol
Benzyl—Resorcinol
Phenylethyl—Resorcinol
Phenylpropyl—Resorcinol
p-Chlorobenzyl—Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4'-Bromo-2,4-Dihydroxydiphenyl Methane Bisphenolic Compounds Bisphenol A
2,2'-methylene bis (4-chlorophenol)
2,2'-methylene bis (3,4,6-trichlorophenol) (hexachlorophene)
2,2'-methylene bis (4-chloro-6-bromophenol)
bis (2-hydroxy-3,5-dichlorophenyl) sulfide
bis (2-hydroxy-5-chlorobenzyl) sulfide As mentioned above, the oral compositions of this invention may include an effective antiplaque amount of a non-cationic antibacterial agent. These are typically halogenated diphenyl ethers and they include:

Halogenated Diphenyl Ethers 2,4,4'-trichloro-2'-hydroxy-diphenyl ether (Triclosan)
2,2'-dihydroxy-5,5'-dibromo-diphenyl ether.

Halogenated Salicylanilides 5-dibromosalicylanilide
3,4',5-trichlorosalcylanilide
3,4',5-tribromosalicylanilide
2,3,3',5-tetrachlorosalicylanilide
3,3,3',5-tetrachlorosalicylanilide
3,5-dibromo-3'-trifluoromethyl salicylanilide
5-n-octanoly-3'-trifluoromethyl salicylanilide
3,5-dibromo-4'-trifluoromethyl salicylanilide
3,5-dibromo-3'-trifluoro methyl salicylanilide (Flurophene)

Benzoic Esters

Methyl—p-Hydroxybenzoic Ester
Ethyl—p-Hydroxybenzoic Ester
Propyl—p-Hydroxybenzoic Ester
Butyl—p-Hydroxybenzoic Ester

Halogenated Carbanilides 3,4,4'-trichlorocarbanilide
3-trifluoromethyl-4,4'-dichlorocarbanilide
3,3,4'-trichlorocarbanilide The noncationic antibacterial agent is present in the oral composition in an effective antiplaque amount, typically about 0.01–5% by weight, preferably about 0.03–1% and more preferably about 0.3–0.4%. The antibacterial agent is substantially water-insoluble meaning that its solubility is less than about 1% by weight in water at 25° C. and may be even less than about 0.1%.

The preferred halogenated diphenyl ether is triclosan.

The oral compositions may also contain an anticaries amount of a fluoride ion source sufficient to supply about 25 ppm to 5000 ppm of fluoride ions.

The sources of fluoride ions, or fluoride-providing component are well known in the art as anti-caries agents. These compounds may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, for example sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, ammonium fluorozirconate, sodium monofluorphosphate, aluminum mono-and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be the present in an amount of about 0.1–3%, more typically about 0.76%.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Suitable sweetening agents include sucrose, lactose, maltose, sorbitol, xylitol, sodium cyclamate, perillartine, AMP (aspartyl phenyl alanine, methyl ester), saccharine and the like. Suitably, flavor and sweetening agents each or together comprise from about 0.1% to 5% more of the preparation.

In the preferred practice of this invention on oral compositions containing the active ingredients of the present invention it is preferably administered to the oral cavity, such as rinsing with the mouthrinse every day or every second or third day or preferably from 1 to 3 times daily, at a pH of about 3 to about 9, generally about 5.5 to about 8, preferably about 6 to 8, for at least 2 weeks up to 8 weeks or more up to lifetime.

The liquid compositions of the present invention are typically prepared by mixing together the ingredients using simple blending procedure with the aqueous vehicle in a suitable vessel.

The solid compositions of this invention can be prepared as lozenges, or as chewing gum or other products, e.g. by stirring the ingredients into a warm gum base or candy base, illustrative of which may be mentioned jelutong, rubber latex, vinylite resins, etc., optionally with conventional plasticizers, softeners, sugar or other sweeteners or carbohydrates such as glucose, sorbitol and the like.

In a commercial embodiment of the present invention the oral compositions of the present invention are sold or distributed in suitable labelled packages, e.g., bottles for mouthrinse, collapsible tubes for toothpaste and the like.

The following examples are further illustrative of the nature of the present invention, but it is understood that the invention is not limited thereto. All amounts and proportions referred to herein and in the appended claims are by weight, unless otherwise indicated. The term "Phenolic flavors" used hereinafter denotes a mixture of 35% eucalyptol, 27% thymol, 21% methyl salicylate and 17% menthol.

EXAMPLE 1

An oral mouthwash is prepared by mixing together:

| | |
|---|---|
| sorbitol | 10% |
| glycerine | 10% |
| betaine (35% aq) | 1.42%, |
| ethanol | 10% |
| propylene glycol | 7.0% |
| Phenolic flavors | 0.15% |
| Triclosan | 0.06% |
| Water, a sufficient amount to make 100% | |

EXAMPLE 2

| | |
|---|---|
| sorbitol | 10% |
| glycerine | 10% |
| betaine (35% aq) | 0.857% |
| ethanol | 10% |
| propylene glycol | 7.0% |
| Phenolic flavors | 0.15% |
| Triclosan | 0.06% |
| Water, a sufficient amount to make 100% | |

EXAMPLE 3

The effects of mouth rinses on dental plaque formation in vitro.

The antiplaque efficacy of the formulation was tested in an in vitro model of dental plaque using procedures described in the American Journal of Dentistry, Vol. 3, Special Edition Sept. 1990, i.e., the flow cell system. The test cells were treated with the rinses (shown in Examples 3 and 4) four times in a 48 hour period. The effects of the rinses were compared to a vehicle control rinse.

| Sample | % plaque reduction |
| --- | --- |
| Example 1 rinse | 37.1% |
| Example 2 rinse | 68.6% |

In the above Example 1, it contains about 0.5% betaine and in Example 2, it contains about 0.7% betaine.

EXAMPLE 4

The effects of the mouth rinses on human dental plaque formation.

A human clinical study was also conducted to measure the effect of an triclosan/cocoamidopropyl betaine/phenolic flavor mouth rinse on dental plaque formation. Ten healthy adults were asked to use the experimental rinses, twice per day for 4 consecutive days, in a cross-over design clinical study. The subjects were given an initial cleaning prophylaxis at the beginning of the study. No other oral hygiene was allowed during the 4 day experimental period. Effects of the rinse treatments were compared to a water control.

| Sample | % plaque reduction |
| --- | --- |
| Example 1 rinse | 31% |
| Example 2 rinse | 32% |

EXAMPLE 8

Mouthrinses containing the following formulations were prepared and a plaque reduction study were initiated over a 4-day period in human volunteers, in accordance with the protocol described in Example 4. The data from the study are also summarized below:

| Treatment | Surfactant | Plaque Score |
| --- | --- | --- |
| Control | water | 1.17 ± 0.20 |
| Control | anionic (0.25% SLS) | 1.19 ± 0.15 |
| phenolic flavors 0.15% 0.06% triclosan/ | 0.25% SLS*/0.2% tauranol | 1.17 ± 0.18 |
| 0.15% phenolic 0.06% triclosan/ | 0.25% SLS*/0.2% tauranol | 1.21 ± 0.14 |
| 0.15% phenolic 0.06% triclosan/ | 0.30% SLS*/0.2% tauranol | 1.12 ± 0.13 |
| 0.15% phenolic 0.06% triclosan/ | 0.3% betaine | 1.00 ± 0.10 |
| 0.15% phenolic | 0.5% betaine | 1.04 ± 0.10 |

*SLS = sodium lauryl sulfate

From the above data, it clearly shows that the combination of phenolics with triclosan with an amphoteric surfactant, i.e., betaine, is superior to triclosan and phenolics in an anionic system, i.e., sodium lauryl sulfate and tauranol.

What is claimed is:

1. In an improved method for managing or controlling dental plaque formation on tooth surfaces comprising treating tooth surfaces with an oral composition of the combination of an effective antimicrobial amount of a blend of phenolic agents, a substantially water-insoluble noncationic antibacterial agent and a surfactant which provides superior antiplaque effect compared to an anionic surfactant system wherein the improvement comprises employing an effective surface tension reducing mount of betaine as surfactant in said oral composition to provide superior antiplaque effectiveness.

2. An oral composition as defined in claim 1 in which said betaine is present in an amount to about 2% w/v when the vehicle is a toothpaste, a tooth powder, or a gel dentifrice.

3. An oral composition according to claim 1 when the vehicle is a mouthrinse or mouthwash, said betaine is present in an mount of about from 0.3% w/v to about 0.5% w/v.

4. An oral composition according to claim 1 wherein said antibacterial antiplaque agent is a member selected from the group consisting of halogenated diphenyl ethers, halogenated salicylanilide benzoic ester and halogenated carbanilides.

5. An oral composition according to claim 1 wherein said halogenated diphenyl ether is 2,4,4'-tricholoro-2'-hydroxydiphenyl ether.

6. An oral composition according to claim 1 wherein said antibacterial antiplaque agent is present from about 0.01% w/v to about 1.0% w/v.

7. An oral composition according to claim 1 in which the phenolic agents comprise eucalyptol, thymol methyl salicylate and menthol, each present in amount at least about 5% by weight of the total blend of phenolic agents.

8. An oral composition according to claim 7 in which the phenolic agents comprises a mixture of about 35% eucalyptol, about 27% thymol, about 21% methyl salicylate and about 21% menthol.

9. An oral composition according to claim 1 which has a pH of about 3 to about 9.

10. An oral composition according to claim 1 which contains about 0.0005% to about 3% of a fluoride-providing compound.

11. An oral composition according to claim 1 in which said betaine is cocoamidopropyl betaine.

* * * * *